United States Patent [19]

Lonsdale et al.

[11] Patent Number: 4,917,800

[45] Date of Patent: Apr. 17, 1990

[54] FUNCTIONAL, PHOTOCHEMICALLY ACTIVE, AND CHEMICALLY ASYMMETRIC MEMBRANES BY INTERFACIAL POLYMERIZATION OF DERIVATIZED MULTIFUNCTIONAL PREPOLYMERS

[75] Inventors: Harold K. Lonsdale, Bend; Carl C. Wamser, West Linn, both of Oreg.

[73] Assignee: Bend Research, Inc., Bend, Oreg.

[21] Appl. No.: 221,307

[22] Filed: Jul. 19, 1988

Related U.S. Application Data

[62] Division of Ser. No. 883,043, Jul. 7, 1986, Pat. No. 4,784,736.

[51] Int. Cl.[4] .............................................. B01D 13/00
[52] U.S. Cl. ...................................... 210/490; 264/49
[58] Field of Search ................. 210/490, 654; 264/49; 204/157.15, 157.6; 540/122, 145

[56] References Cited

U.S. PATENT DOCUMENTS 4,784,736  11/1988  Lonsdale et al. ............ 204/157.6 X

*Primary Examiner*—Frank Spear
*Attorney, Agent, or Firm*—Chernoff, Vilhauer, McClung & Stenzel

[57] ABSTRACT

The preparation of a novel class of thin film membranes by interfacial polymerization is disclosed, said membranes incorporating as part of their polymeric structure the functionality of monomeric or oligomeric precursors. Specific embodiments include porphyrin and phthalocyanine derivatives that are photochemically or electrochemically active, as well as chemically asymmetric membranes.

18 Claims, No Drawings

FUNCTIONAL, PHOTOCHEMICALLY ACTIVE, AND CHEMICALLY ASYMMETRIC MEMBRANES BY INTERFACIAL POLYMERIZATION OF DERIVATIZED MULTIFUNCTIONAL PREPOLYMERS

The government has rights in this invention under Department of Energy Contract No. DEFGO68-5ER13389.

This application is a division of application Ser. No. 883,043, filed Jul. 7, 1986, now U.S. Pat. No. 4,784,736.

This invention has to do with novel ultrathin functional nonporous permeable membranes and methods of making the same. Such membranes combine the high transport rates needed in certain membrane processes with the specificity that can be introduced through selective functionality.

BACKGROUND OF THE INVENTION

Membranes are selective barriers that allow certain chemical species to pass while retaining others. As such, they are useful in a wide variety of separation processes, including reverse osmosis, dialysis, electrodialysis, ultrafiltration, and gas separations. These processes and others are fully described in Volume VII of the "Techniques of Chemistry" series entitled "Membranes in Separations" (1975) by Hwang and Kammermeyer. In all membrane separation processes, the transmembrane flux is a key criterion in determining the cost of the process. High flux is generally associated with thin membranes, in keeping with Fick's first law, and considerable research and development has been expended over the past 20 years or so toward making very thin, yet still highly selective membranes. The first technical breakthrough was the reverse osmosis membrane invented by Leob and Sourirajan and disclosed in U.S. Pat. No. 3,133,132. Numerous types of membranes have been made since then using the Loeb-Sourirajan technique. See, for example, Kesting, 50 Pure & Appl. Chem. 633 (1978), who discloses asymmetric (skinned) cellulosic membranes, and Broens et al., 32 Desalination 33 (1980), who disclose similar membranes cellulose acetate, polysulfone, polyacrylonitrile, and polydimethylphenyleneoxide.

The second breakthrough in making thin, selective membranes was due primarily to Cadotte. Cadotte borrowed from the teachings of Morgan, who first described in detail "interfacial polymerization." Interfacial polymerization (IP) is a process in which a very thin film (or membrane) can be made by reacting two monomers at the interface between two immiscible solutions. It is best described by example. "Nylons" are a class of polymer referred to as polyamides. They are made, for example, by reacting a diacid chloride, sucyh as adipoyl chloride, with a diamine, such as hexamethylene diamine. That reaction can be carried out homogeneously in a solution to produce the polymer in resin form. However, it can also be carried out at an interface by dissolving the diamine in water and floating a hexane solution of the diacid chloride on top of the water phase. The diamine reacts with the diacid chloride at the interface between these two immiscible solvents, forming a polyamide film at the interface which is rather impermeable to the reactants. Thus, once the film forms, the reaction slows down drastically, so that the film remains very thin. In fact, if the film is removed from the interface by mechanical means, fresh film forms at the interface, because the reactants are so highly reactive with one another.

Cadotte used such knowledge of interfacial polymerization techniques to produce extremely thin, supported membranes such as are disclosed in U.S. Pat. No. 4,277,344. As a modification of the two immiscible liquid phases, he dissolved one reactant in a solvent and then used that solution to fill the pores of a microporous substrate membrane. He then exposed that wet membrane to a second, immiscible solvent containing the other reactant. An interfacially polymerized, very thin film formed at the surface of the microporous substrate, which then served as a support for the very thin membrane. Numreous adaptations of the Cadotte-type membranes have been made using essentially the same IP method.

Morgan, in Volume 20 of the "Polymer Reviews" series entitled "Condensation Polymers: By Interfactial and Solution Methods" (1965), describes numerous condensation reaction chemistries that can be used to make polymers interfacially. Among the important chemistries are: polyamides, as already described; polyureas, polyurethanes, polysulfonamides, and polyesters; several other less important classes are also described. Morgan and others have also described the conditions important to making continuous, thin interfacial films: temperature, the nature of the solvents and co-solvents, the concentrations of the two reactants, and the reactivity of the two monomers. Id. at pages 486–509. Refinements of the art developed over the past 20 years include the use of "blocked" or protected monomers that can be later unblocked to alter the chemistry of the finished film or membrane, the use of post-treatment of the films to alter their chemistry, and the use of heteratoms in the monomers to alter the properties of the final film or membrane. In the classical organic chemistry sense, these alterations would be referred to as changes in the functionality i.e., in the available functional groups of the monomers and/or polymers.

SUMMARY OF THE INVENTION

According to the present invention there is provided a different kind of functionality. By "functionality" is meant the state of being chemically (including photochemically or electrochemically) selectively reactive; the term is not intended to include chemical reactivity owing to the presence of one or more free and unreacted functional groups in the classic organic chemistry sense, such as a vinyl group, a hydroxyl group or a carboxyl group. It has been found that the interfacial polymerization method can be used to produce ultrathin membranes that contain such functionality as defined herein as an integral part of the polymeric membrane, such that the ultimate membrane retains substantially the same specific functionality of the original prepolymeric (monomeric or oligomeric) moiety. The interfacial polymerization method of the present invention provides means for incorporation of that functional prepolymeric moiety into a polymeric membrane without substantially altering its functionality, thus endowing the membrane with that same functionality. Thus, in a sence, the present invention may be regarded as a method of chemically binding a selectively reactive moiety within a polymeric matrix, while at the same time leaving that moiety available to enter into its characteristic reactions.

Preparation of such ultrathin "functional" membranes is essentially a two-step process comprising the steps of:

(1) forming, if necessary, polymerizable derivatives of a discrete prepolymeric molecule possessing "functionality;" and (2) forming by IP a membrane of the derivatives of the molecule so as to imbue the so-formed membrane with substantially the same "functionality" as possessed by the original prepolymeric molecule.

The following representational chemical reaction schemes summarize the present invention:

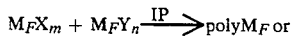

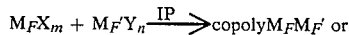

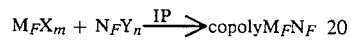

where $M_F$ and $M_F'$ are different prepolymeric (monomeric or oligomeric) molecules or moieties with a given functionality such as a selective transport agent; $N_F$ is any linkable or crosslinkable prepolymeric molecule or moiety that does not contain such functionality; X and Y are chemically functional groups in the classis organic chemistry sense, such as amines and acid chlorides, which have mutual reactivity allowing them to undergo interfacial polymerization; m and n are integers $\geq 2$; IP stands for an interfacial polymerization reaction; poly$M_F$ is an interfacially polymerized polymer containing discrete repeating units of the functional moiety $M_F$; copoly$M_F M_F'$ is an interfacially polymerized copolymer containing discrete repeating units of the functional moieities $M_F$ and $M_F'$; and copoly$M_F N_F$ is an interfacially polymerized copolymer containing discrete repeating units of the functional moiety $M_F$ and of the non-functionality-containing moiety $N_F$.

When necessary, the conversion of the original prepolymer, for example $M_F$, into the needed polymerizable prepolymeric derivatives, $M_F X_m$ or $M_F Y_n$, is carried out by standard synthetic techniques in such a way as to retain the special functionality of $M_F$. The required synthetic techniques will necessarily be different for the various types of X and Y groups which could be used and may also have to be modified to assure that the functionality of $M_F$ can be retained. Specific examples of the X and Y mutually reactive groups include amines and acid halides (to form polyamides), alcohols and acid halides (to form polyesters), thiols and acid halides (to form polythioesters), amines and isocyanates (to form polyureas), alcohols and isocyanates (to form polyurethanes), and amines and sulfonyl halides (to form polysulfonamides). Other lesser known but potentially useful examples of condensation reaction types are set forth in Chapter 9 of Morgan, "Condensation Polymers: By Interfacial and Solution Methods" (1965).

DETAILED DESCRIPTION OF THE INVENTION

According to the present invention, thin film membranes containing "functionality" as defined herein mey be prepared by interfacial polymerization methods. The term "membranes" is meant to include thin film, generally planar shapes, hollow fibers, microcapsules, and beads.

ARTIFICIAL PHOTOSYNTHESIS MEMBRANES

In one embodiment of the present invention, thin films on the order of 20 to 1000 nanometers may be prepared from porphyrins or related derivatives. These membranes have a novel combination of properties that make then useful in so-called "artificial photosynthesis" or, more specifically, photoelectrochemical production of fuels. In this process, photons in solar radiation are absorbed by a material that can convert the energy of the photons to an electron flow. Among the best organic matreials known today for this application are a class of chemical substances known as porphyrins. A porphyrin molecule, the structure of which is shown below, possesses "functionality" in the context of the present invention in that is can absorb energy from light and subsequently initiate photochemical electron transfer, oxidation and/or reduction reactions.

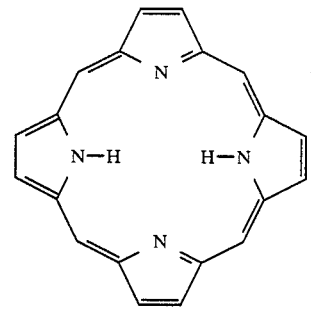

Substituted derivatives of the parent porphyrin molecule which are well characterized include tetraphenylporphyrin, tetratolylporphyrin, tetracarboxyphenylporphyrin, tetrapyridylporphyrin, tetramethylpyridiniumporphyrin, tetrasulfonatophenylporphyrin, uroporphyrin, etioporphyrin, coproporphyrin, mesoporphyrin, protoporphyrin, deuteroporphyrin, pyrroporphyrin, octaethylporphyrin, tetrabenzoporphyrin, hematin, heme, hemin and chlorophyll. Phthalocyanine, shown below, and its derivatives are also useful analogs of porphyrins for purposes of the present invention.

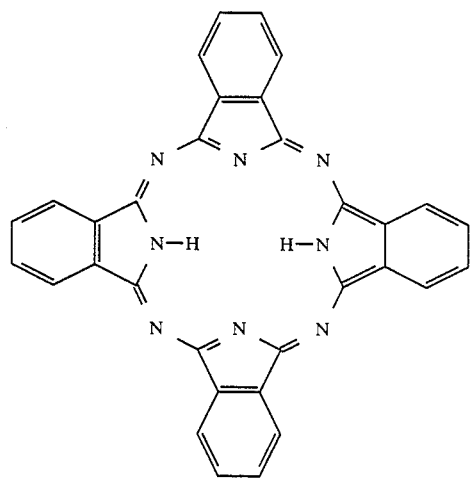

To make a photoelectrochemical device, a very tin film of polyporphyrin that contains a high density of porphyrin moieties is needed. The film must be thin in order to conduct photogenerated electrons without significant recombination of electrons and electron "holes," yet it must be sufficiently dense in porphyrin to intercept most of the photons impinging on it. Such a film can be made utilizing conventional interfacial polymerization techniques involving condensation reactions between pairs of mutually chemically reactive groups. Thus, with respect to derivatized porphyrins, the method works as to two mutually reactive monomers of the formula

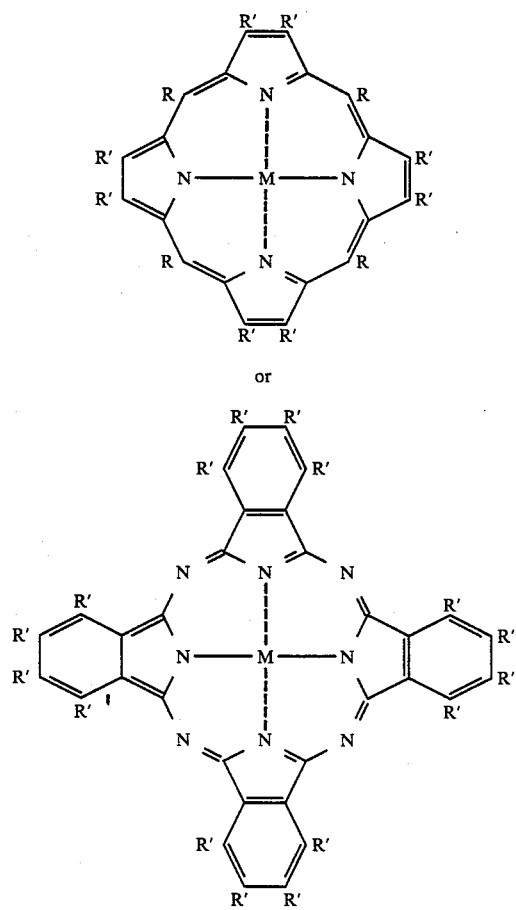

wherein
M is a metal ion or —H H—,
R is H, alkyl, aryl, pyridinyl, R', alkyl-R', or aryl-R'
R' is H, Hal, $NH_2$, $CH_2NH_2$, SH, OH, COHal, COOH, NCO, or $SO_2Hal$, and
Hal is halide
and wherein the IP condensation reaction is selected from the reaction of (a) amines and acid halides (to form polyamides), (b) alcohols and acid halides (to form polyesters), (c) thiols and acid halides (to form polythioesters), (d) amines and isocyanates (to form polyureas), (e) alcohols and isocyanates (to form polyurethanes), and (f) amines and sulfonyl halides (to form polysulfonamides).

In many cases, such polymeric porphyrin membranes will be chemically asymmetric with respect to the opposite sides of the membrane layer. For example, in the case of polycondensation by IP of amines and acid halides to bind the porphyrin molecules together by polyamide linkages, the surface of the membrane formed which isin contact with the aqueous phase of the reaction environment containing the amine-substituted porphyrin will tend to predominate in unreacted amine functionalities, while the membrane surface in contact with the organic phase containing the acid chloride-substituted porphyrin will tend to predominate in unreacted acid chloride groups, which, upon hydrolysis, become carboxyl groups. See Enkelmann and Wegner, 21 *J. Appl. Polm. Sci.* 997 (1977). This asymmetry makes the resulting membrane particularly well-suited for use in artificial photosynethesis inasmuch as the porphyrins throughout the membrane will exhibit a gradient of redox potentials that can be utilized to provide a driving force for the directional transport of electrons through the membrane. Porphyrin redox potentials are calculable based upon the particular substituents attached to each porphyrin moiety using the Hammett Equation, as was shown by Kadish in 98 JACS 3326 (1976). In the assymmetric polyamide-linkage-containing polyporphyrin under consideration, the substituents include amine, amide and carboxyl groups in a distribution that follows a gradient across the membrane, resulting in a gradient of redox potentials across the membrane. The magnitude and direction of such a redox potential gradient can be adjusted by either the incorporation of metals in the surface porphyrins or by pH adjustment of solutions present on either side of the membrane.

EXAMPLES

Polyporphyrin membranes were prepared according to the general reaction scheme shown above by reacting an acid chloride porphyrin (structure IA below) with a polyamine directly on one surface of a microporous support, such that the support became an integral part of the membrane. In some cases, the polyamine was another porphyrin derivative (structure IIA or IIB below), and in other cases, aliphatic polyamines were used, including
ethylene diamine (EDA)
diethylenetriamine (DET)
1,4-bis(3-aminopropyl)piperazine (BAPP)
N,N'-bis(3-aminopropyl)ethylene diamine (BAPED)
3,3'-diamino-N-methyldipropylamine (DAMD).

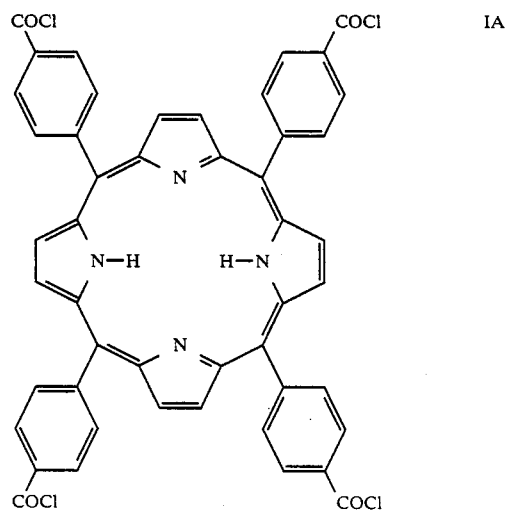

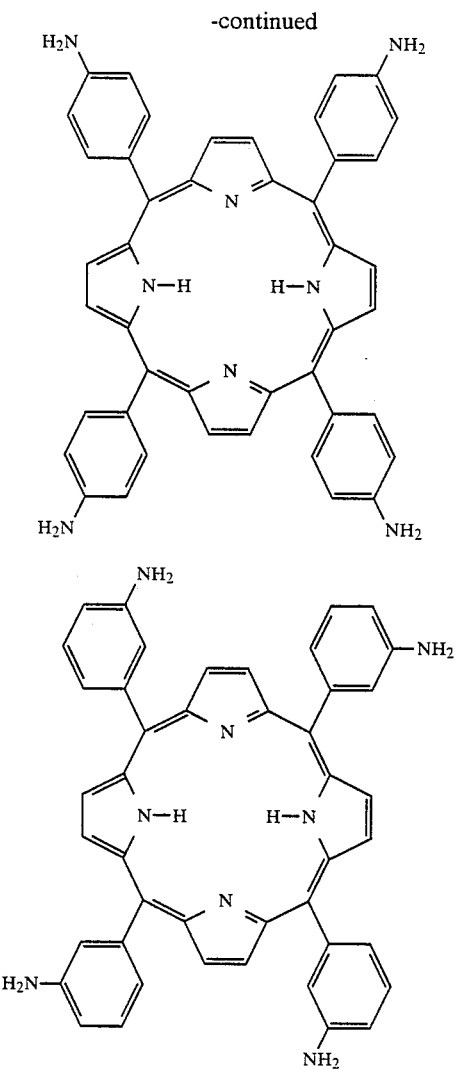

First, a reservoir of one of the two interfacial reactants was provided by filling the pores of a circular plug (1-inch diameter by ⅛-inch thick) of porous polyethylene (Porex X-4719 filter made by Porex Technologies of Atlanta, Georgia) set in an annular ring of slightly larger inside diameter. Typically, the reservoir solution comprised about 2 ml of a dilute solution of the acid chloride porphyrin IA in a water-immiscible organic solvent that was simply pipetted onto the plug, thereby wetting the plug. Acid chloride concentration was typically $10^{-2}$M or less, and the solvent was usually chloroform, although dichloromethane, 1,1,2,2,-tetrachloroethane, or 1,1,2,3,3-pentachloropropane was also used.

Next, the microporous support (Celgard 2400 polypropylene, with roughly ellipsoidal-shaped pores measuring about 20 nanometers by 200 nanometers on each axis made by Celanese Corp. of Charlotte, N.C.) was laid over the top of the wetted porous polyethylene plug; the organic solution was wicked up into the microporous support from the reservoir below. A second annular ring was then placed atop the microporous support, forming a second reservoir that was filled with an aqueous solution of the polyamine. Amine concentration varied from $10^{-1}$M to $10^{-4}$M for the nonporphyrin amines and from $10^{-3}$ M to $10^{-6}$ M for the porphyrin amines IIA and IIB. The interfacial polymerization reaction was allowed to proceed for a period of 2 minutes to 16 hours, usually 5 to 60 minutes. The reaction was stopped by removing the upper aqueous layer and the upper annular ring. The so-formed polyporphyrin thin-film composite (TFC) membrane was removed from the apparatus. To verify that the interfacial polymerization reaction had actually occurred, the upper and lower surfaces of the membrane were thoroughly washed by soaking in solvents known to dissolve one or both of the monomers for a period of several minutes to as long as one week (30 minutes was usually found to be sufficient). Such solvents included water, chloroform, and dimethylsulfoxide used sequentially, although in some cases only water and chloroform washes were necessary. The washes removed unreacted monomer from the membrane surfaces, evidenced by the appreanace of color in the wash solution (identified as the characteristic visible absorption spectrum of the particular porphyrin). The washes were considered complete when no further monomer was removed by the washing. Examination of the intact washed membranes under a scanning electron microscope at 700× confirmed the existence of the interfacially polymerized membrane.

Polyporphyrin membranes formed in this way were found to be extremely thin, with thicknesses ranging from 0.07 to 0.8 micrometers (70 to 800 nanometers), depending on reaction time, reactant concentrations, and other reaction conditions. The ultraviolet-visible absorption spectra in the 310 nm–750 nm range of such membranes were determined by spectrophotometric analysis relative to a reference of an identical but untreated smaple of microporous support. By comparing the so-measured absorption spectra of the membranes with the known spectra of solar radiation, it was calculated that the membranes could absorb a significant fraction of the incident solar spectrum at the earth's surface, up to 30% of the total energy present in solar radiation. Film thicknesses of the IP-formed polyporphyrin film portion of the composite membranes were calculated from the measured weight, divided by the measured area and density (assumed to be 1 g/cc). Measured weight comprised the difference between the original dry micorporous support before reaction, and the finished TFC membrane after reaction, solvent washing, and air drying to constant weight. The results are set forth in the Table.

The polyporphyrin membrane formed by the reaction of the two porphyrin monomers shown by structures IA and IIA has the idealized structure shown below. The structure shown illustrates the asymmetry of the two surfaces, in that one surface contains an excess of amine groups and the other surface contains an excess of acid chloride groups, which could later be hydrolyzed to carboxylic acid groups.

TABLE

| $M_FX_m$ | $M_FY_n$ | $N_FY_n$ | Polymerization Time (minutes) | Thickness (nm) | Percent[a] Absorption |
|---|---|---|---|---|---|
| IA($10^{-4}$M)[b] | IIA($10^{-4}$M)[b] | — | 1000 | 760 | 26 |

TABLE-continued

| $M_FX_m$ | $M_FY_n$ | $N_FY_n$ | Polymerization Time (minutes) | Thickness (nm) | Percent[a] Absorption |
|---|---|---|---|---|---|
| IA($10^{-3}$M) | IIA($10^{-4}$M)[b] | — | 1000 | 840 | 30 |
| IA($10^{-3}$M) | — | DET($10^{-2}$M) | 2 | 130 | 9 |
| IA($10^{-3}$M) | — | DET($10^{-2}$M) | 5 | 310 | 13 |
| IA($10^{-3}$M) | — | DET($10^{-2}$M) | 20 | 480 | 19 |
| IA($10^{-3}$M) | — | DET($10^{-2}$M) | 60 | 680 | 26 |
| IA($10^{-3}$M) | — | EDA(.05M) | 30 | 280 | 16 |
| IA($10^{-3}$M) | — | EDA($10^{-2}$M) | 15 | 230 | 12 |
| IA($10^{-3}$M) | — | BAPP(.005M) | 30 | 540 | 23 |
| IA($10^{-3}$M) | — | BAPP($10^{-2}$M) | 30 | 570 | 23 |
| IA($10^{-3}$M) | — | BAPED($10^{-3}$M) | 30 | 120 | 8 |
| IA($10^{-3}$M) | — | BAPED(.05M) | 15 | 540 | 23 |
| IA($10^{-3}$M) | — | DAMD(.005M) | 60 | 650 | 29 |
| IA($10^{-3}$M) | — | DAMD(.005M) | 10 | 430 | 19 |

[a] based upon total incident solar energy
[b] rounded to nearest order of magnitude amine side—excess tetra(p-aminophenyl)porphyrin (IIA) in aqueous solution

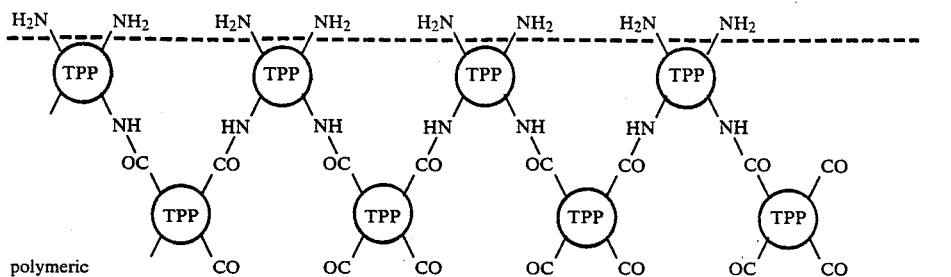

polymeric porphyrin membrane

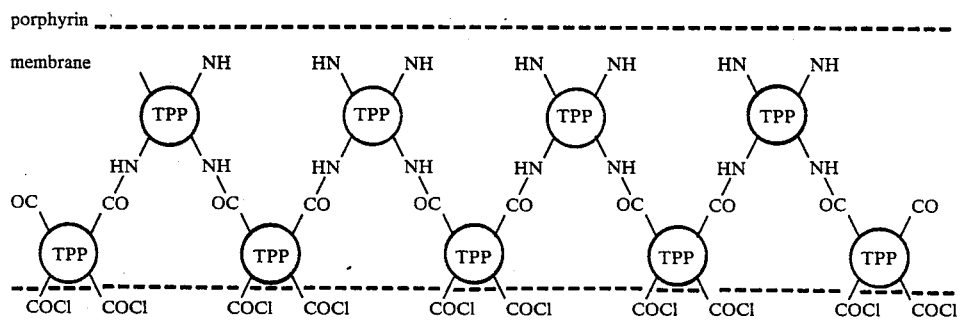

acid chloride side—excess tetra(p-chlorocarbonylphenyl) porphyrin (IA) in organic solution Increasing the number of functional groups present on the porphyrin monomers makes the film highly crosslinked, and thus relatively strong. In most cases, however, the ultrathin film should be supported on a support of some kind, most preferably a microporous support such as polysulfone, polyethersulfone, cellulose, cellulose acetate, polytetrafluoroethylene, polyamide, polyester, polyethylene, polypropylene, or poly(vinylidenefluoride) having pores comparable in size to the thickness of the membrane. The support itself may take virtually any shape, including that of hollow fibers, thin films, beads, and microcapsules. When so supported, the interfacial polymerization of the functional moieties may take place within the surface pores of the support, as taught by Cadotte in U.S. Pat. No. 4,277,344. Such a supported film can then be used to capture photons, producing photoelectrons. If the film is in contact with appropriate solutions on each side of the membrane, these photoelectrons, properly directed, can be used to carry out separate oxidation and reduction reactions on opposite sides of the membrane. In one possible application, these redox reactions may then be used to "split" water to produce hydrogen and oxygen. Hydrogen, of course, is a fuel, and oxygen has widespread application in industry, medicine, and science.

The interfacial polymerization method can also be used to produce thin, functional membranes for use in a host of other applications, including in organic semiconductors, biosensors, heparinized surfaces, facilitated transport membranes utilizing crown ethers and other carriers, targeted drug delivery including membrane-bound antigens, catalyst-containing membranes, treated surfaces, sharpened resolution chromatographic packing materials, and narrow band optical absorbers.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. A thin film composite membrane comprising a microporous polymeric membrane support and an ultrathin membrane comprising the interfacial polymerization reaction product made from at least one prepolymer of the type $M_FX_m$, $M_F'Y_n$ and $N_FY_n$ wherein $M_F$ and $M_F'$ are monomeric or oligomeric moieties that can initiate photochemical redox reactions, $N_F$ is a linkable or crosslinkable monomeric or ologiomeric moiety that cannot initiate photochemical redox reactions, X and Y are groups which render said prepolymers reactive in an interfacial polymerization reaction, m and n are integers $\geq 2$, and wherein said interfacial polymerization reaction product possesses substantially the same selective photochemical redox reactivity as $M_F$ and $M_F'$.

2. The thin film composite membrane of claim 1 wherein $M_F$ and $M_F'$ are selected from the group consisting essentially of porphyrins and phthalocyanines and derivatives thereof.

3. A composition of matter comprising the interfacial polymerization reaction product of monomers that are mutually reactive in a condensation reaction, at least one of said monomers being of the formula

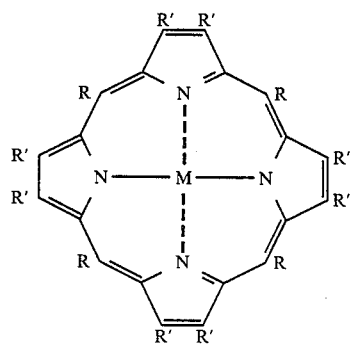

or

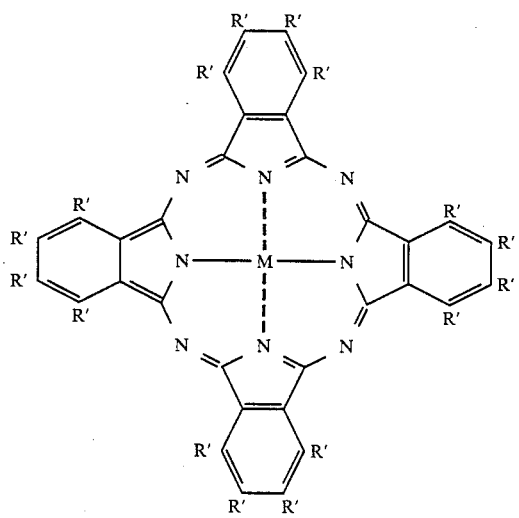

wherein
M is a metal ion or —H H—,
R is H, alkyl, aryl, pyridinyl, R', alkyl-R', or aryl-R',
R' is H, Hal, NH$_2$, CH$_2$NH$_2$SH, OH, COHal, COOH, NCO, or SO$_2$Hal, and
Hal is a halide.

4. A thin film composite membrane comprising a micorporous polymeric membrane support and an ultrathin membrane comprising the interfacial polymerization reaction product of monomers that are mutually reactive in a condensation reaction, at least one of said monomers being of the formula

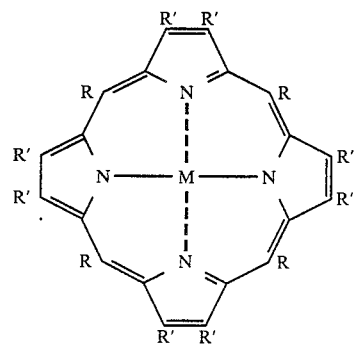

or

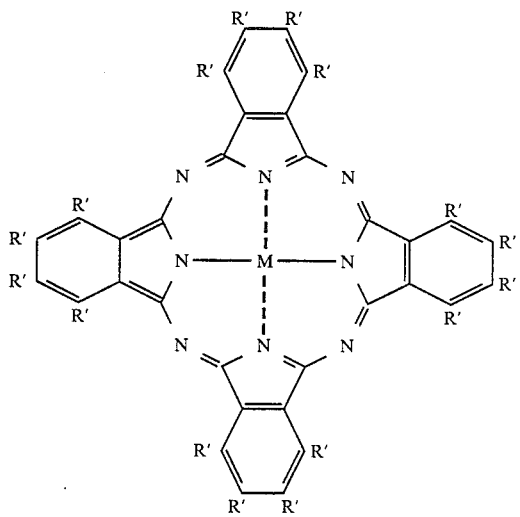

wherein
M is a metal ion or —H H—,
R is H, alkyl, aryl, pyridinyl, R',
alkyl-R', or aryl-R',
R' is H, Hal, NH$_2$, CH$_2$NH$_2$, SH, OH, COHal, COOH, NCO, or SO$_2$Hal, and
Hal is a halide.

5. The composition of matter of claim 1 wherein the form of said interfacial polymerization reaction product is an ultrathin film chemically asymmetric membrane wherein there is a predominance of X groups of hydrolyzed X groups at or near one surface of said membrane and a predominance of Y groups of hydrolyzed Y groups at or near the other surface of said membrane.

6. The composition of matter of claim 3 wherein the form of said interfacial polymerization reaction product is an ultrathin film chemically asymmetric membrane wherein said membrane contains a predominance of one type of R' group or hydrolyzed R' group at or near one surface of said membrane and a predominance of another type of R' group or hydrolyzed R' group at or near the other surface of said membrane.

7. The composition of matter of claim 5 or 6 wherein in the form of said interfacial polymerization reaction product is an ultrathin film chemically asymmetric membrane wherein said membrane has a predominance of one electrical charge on one surface of said membrane and a predominance of the opposite electrical charge on the other surface of said membrane.

8. A method of making a polymer containing recurring linked and crosslinked groups selected from $M_F$ and $M_F'$ wherein $M_F$ and $M_F'$ are prepolymeric moieties that can initiate photochemical redox reactions, comprising:
(a) forming a first solution of $M_F X_m$ in a first liquid;
(b) forming a second solution containing a second prepolymeric compound selected from $M_F X_n$, $M_F' Y_n$ and $N_F Y_n$ in a second liquid which is immiscible with said first liquid;
(c) combining said first and second solutions so as to form an interface between the two; and
(d) reacting $M_F X_m$ and said second prepolymeric compound at the interface of said first and second solutions wherien X and Y are different groups which are mutually reactive in an interfacial polymerization reaction, $N_F$ is a linking or a crosslinking group, and m and n are integers $\geq 2$.

9. The method of claim 8 wherien said interfacial polymerization reaction is a condensation reaction.

10. The method of claim 8 wherein X and Y are selected from $NH_2$, $CH_2NH_2$, SH, OH, COHal, COOH, NCO and $SO_2Hal$, and Hal is halide.

11. The method of claim 8 wherein $M_F$ is selected from the group consisting of porphyrins and phthalocyanines and derivatives thereof.

12. The method of claim 8 wherein the interface between said first and second solutions is at the surface pores of a microporous polymeric membrane support.

13. The method of claim 8 wherein the form of the polymer made is an ultrathin film chemically asymmetric membrane containing a predominance of X groups or hydrolyzed X groups at or near one surface of said membrene and a predominance of Y groups or hydrolyzed Y groups at or near the other surface of said membrane.

14. THe method of claim 13 wherein said ultrathin film chemically asymmetric membrane has a predominance of one electrical charge on one surface of said membrane and a predominance of the opposite electrical charge on the other surface of said membrane.

15. A method of making a polymer containing recurring linked and crosslinked groups of porphyrins, phthalocyanines and derivatives thereof comprising:
(a) forming a first solution of a first reactive compound of the formula

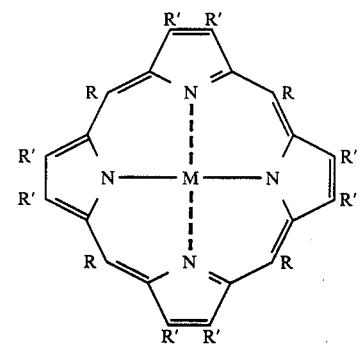

or

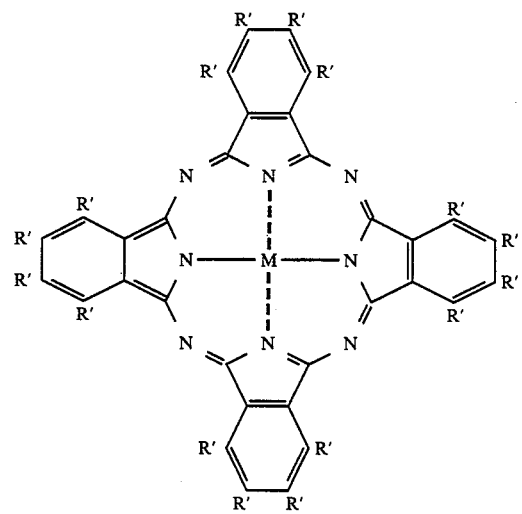

wherein
M is a metal ion or —H H—,
R is H, alkyl, aryl, pyridinyl, R', alkyl-R', or aryl-R',
R' is H, Hal, $NH_2$, $CH_2NH_2$, SH, OH, COHal, COOH, NCO, or $SO_2Hal$, and
Hal is halide;
(b) forming a second solution of a second reactive compound that is reactive with said first reactive compound in an interfacial polymerization reaction, said second solution being immiscible with said first solution;
(c) combining said first and second solutions so as to form an interface between the two; and
(d) reacting said first and second reactive compounds at the interface of said first and second solutions.

16. The method of claim 15 wherein the interface between said first and second solutions is at the surface pores of a microporous polymeric membrane support.

17. The method of claim 15 wherein the form of the polymer made is an ultrathin film chemically asymmetric membrane containing a predominance of one type of R' group or hydrolyzed R' group at or near one surface of said membrane and a predominance of another type of R' group or hydrolyzed R' group at or near the other surface of said membrane.

18. The method of claim 17 wherein said ultrathin film chemically asymmetric membrane has a predominance of one electrical charge on one surface of said membrane and a predominance of the opposite electrical charge on the other surface of said membrane.

* * * * *

UNITED STATES PATENT AND TRADEMARK OFFICE
CERTIFICATE OF CORRECTION

PATENT NO. : 4,917,800                               Page 1 of 3
DATED : April 17, 1990
INVENTOR(S) : Harold K. Lonsdale, et al.

It is certified that error appears in the above-identified patent and that said Letters Patent is hereby corrected as shown below:

| | | |
|---|---|---|
| Col. 1, | Line 37: | Change "Leob" to --Loeb--. |
| Col. 1, | Line 55: | Change "sucyh" to --such--. |
| Col. 2, | Line 36: | Change "heteratoms" to --heteroatoms--. |
| Col. 2, | Line 64: | Change "sence" to --sense--. |
| Col. 3, | Line 27: | Change "classis" to --classic--. |
| Col. 3, | Line 64: | Change "mey" to --may--. |
| Col. 4, | Line 12: | Change "matreials" to --materials--. |
| Col. 4, | Line 16: | Change "is" to --it--. |
| Col. 4, | Line 66: | Change "tin" to --thin--. |
| Col. 5, | Line 67: | Change "isin" to --is in--. |
| Col. 6, | Line 8: | Change "Polm." to --Polym.--. |
| Col. 7, | Line 54: | Delete "," between "2" and "tetra...". (2nd occurrence) |

UNITED STATES PATENT AND TRADEMARK OFFICE
CERTIFICATE OF CORRECTION

PATENT NO. : 4,917,800                 Page 2 of 3

DATED : April 17, 1990

INVENTOR(S) : Harold K. Lonsdale, et al.

It is certified that error appears in the above-identified patent and that said Letters Patent is hereby corrected as shown below:

Col. 8, Line 23: Change "appreanace" to --appearance--.

Col. 8, Line 39: Change "smaple" to --sample--.

Col. 8, Line 41: Change "spectra" to --spectrum--.

Col. 8, Line 50: Change "micorporous" to --microporous--.

Col. 11, Line 11: Change "ologiomeric" to --oligomeric--.

Col. 12, Line 57: Change "of" to --or--. (2nd occurrence)

Col. 12, Line 59: Change "of" to --or--. (2nd occurrence)

Col. 13, Line 19: Change "$M_F X_n$" to --$M_F Y_n$--.

Col. 13, Line 27: Change "wherien" to --wherein--.

Col. 13, Line 34: Change "wherien" to --wherein--.

UNITED STATES PATENT AND TRADEMARK OFFICE
CERTIFICATE OF CORRECTION

PATENT NO. : 4,917,800

DATED : April 17, 1990

INVENTOR(S) : Harold K. Lonsdale, et al.

It is certified that error appears in the above-identified patent and that said Letters Patent is hereby corrected as shown below:

Col. 13, Line 52: Change "membrene" to --membrane--.

Col. 13, Line 56: Change "THe" to --The--.

Signed and Sealed this

Eleventh Day of June, 1991

Attest:

HARRY F. MANBECK, JR.

*Attesting Officer*  *Commissioner of Patents and Trademarks*